(12) United States Patent
Tanugula et al.

(10) Patent No.: US 10,299,894 B2
(45) Date of Patent: May 28, 2019

(54) TREATMENT PLAN SPECIFIC BITE ADJUSTMENT STRUCTURES

(71) Applicant: Align Technology, Inc., San Jose, CA (US)

(72) Inventors: Rohit Tanugula, San Jose, CA (US); John Morton, San Jose, CA (US); Chunhua Li, Cupertino, CA (US); Bastien Pesenti, San Jose, CA (US); Jihua Cheng, San Jose, CA (US); Jeeyoung Choi, Sunnyvale, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 14/186,799

(22) Filed: Feb. 21, 2014

(65) Prior Publication Data
US 2015/0238283 A1 Aug. 27, 2015

(51) Int. Cl.
*A61C 7/00* (2006.01)
*A61C 7/36* (2006.01)
*A61C 7/08* (2006.01)
*G06F 17/50* (2006.01)

(52) U.S. Cl.
CPC .......... *A61C 7/36* (2013.01); *A61C 7/002* (2013.01); *A61C 7/08* (2013.01); *G06F 17/50* (2013.01)

(58) Field of Classification Search
CPC .............. A61C 7/00; A61C 7/08; A61C 7/36
USPC .................................................. 433/6, 18, 19
See application file for complete search history.

(56) References Cited

U.S. PATENT DOCUMENTS

| 2,467,432 A | 4/1949 | Kesling |
| 3,379,193 A * | 4/1968 | Monsghan ........... A63B 71/085 |
| | | 128/862 |
| 3,407,500 A | 10/1968 | Kesling |

(Continued)

FOREIGN PATENT DOCUMENTS

| AU | 3031677 A | 5/1979 |
| AU | 517102 B2 | 7/1981 |

(Continued)

OTHER PUBLICATIONS

AnotherInvisalignBlog. Invisalign Virtual Bite Ramps. Posted Jun. 17, 2012. 5 pages. Retrieved on Aug. 14, 2013 from http://anotherinvisalignblow.wordpress.com/2012/06/17/invisalign-lingual-power-ridges-photos/.

(Continued)

*Primary Examiner* — Yogesh P Patel
*Assistant Examiner* — Matthew P Saunders
(74) *Attorney, Agent, or Firm* — Wilson Sonsini Goodrich & Rosati

(57) ABSTRACT

A series of appliances including a first shell and a second shell can be designed to incrementally implement a treatment plan. The first and second shells can have cavities designed to receive teeth of a jaw. A first bite adjustment structures can be formed of a same material as the first shell, extending from the first shell and designed to interface with teeth of a second jaw. A second bite adjustment structures can be formed of a same material as the second shell, extending from the second shell and designed to interface with teeth of the second jaw. The first and the second bite adjustment structures can have respective shapes and locations specific to respective stages of the treatment plan.

12 Claims, 11 Drawing Sheets

(56) References Cited

U.S. PATENT DOCUMENTS

| | | | |
|---|---|---|---|
| 3,478,742 A * | 11/1969 | Bohlmann | A61C 7/08 128/860 |
| 3,600,808 A | 8/1971 | Reeve | |
| 3,660,900 A | 5/1972 | Andrews | |
| 3,683,502 A | 8/1972 | Wallshein | |
| 3,738,005 A | 6/1973 | Cohen et al. | |
| 3,860,803 A | 1/1975 | Levine | |
| 3,916,526 A | 11/1975 | Schudy | |
| 3,922,786 A | 12/1975 | Lavin | |
| 3,950,851 A | 4/1976 | Bergersen | |
| 3,983,628 A | 10/1976 | Acevedo | |
| 4,014,096 A | 3/1977 | Dellinger | |
| 4,195,046 A | 3/1980 | Kesling | |
| 4,253,828 A | 3/1981 | Coles et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,419,992 A | 12/1983 | Chorbajian | |
| 4,478,580 A | 10/1984 | Barrut | |
| 4,500,294 A | 2/1985 | Lewis | |
| 4,509,918 A | 2/1985 | Clark | |
| 4,504,225 A | 3/1985 | Yoshii | |
| 4,505,673 A | 3/1985 | Yoshii | |
| 4,526,540 A | 7/1985 | Dellinger | |
| 4,557,692 A * | 12/1985 | Chorbajian | A61C 5/007 433/215 |
| 4,575,330 A | 3/1986 | Hull | |
| 4,575,805 A | 3/1986 | Moermann et al. | |
| 4,591,341 A | 5/1986 | Andrews | |
| 4,609,349 A | 9/1986 | Cain | |
| 4,611,288 A | 9/1986 | Duret et al. | |
| 4,656,860 A | 4/1987 | Orthuber et al. | |
| 4,663,720 A | 5/1987 | Duret et al. | |
| 4,664,626 A | 5/1987 | Kesling | |
| 4,676,747 A | 6/1987 | Kesling | |
| 4,742,464 A | 5/1988 | Duret et al. | |
| 4,755,139 A | 7/1988 | Abbatte et al. | |
| 4,763,791 A | 8/1988 | Halverson et al. | |
| 4,773,853 A * | 9/1988 | Kussick | A61C 7/00 433/6 |
| 4,793,803 A | 12/1988 | Martz | |
| 4,798,534 A | 1/1989 | Breads | |
| 4,836,778 A | 6/1989 | Baumrind et al. | |
| 4,837,732 A | 6/1989 | Brandestini et al. | |
| 4,850,864 A | 7/1989 | Diamond | |
| 4,850,865 A | 7/1989 | Napolitano | |
| 4,856,991 A * | 8/1989 | Breads | A61C 7/125 433/24 |
| 4,877,398 A | 10/1989 | Kesling | |
| 4,880,380 A | 11/1989 | Martz | |
| 4,889,238 A | 12/1989 | Batchelor | |
| 4,890,608 A | 1/1990 | Steer | |
| 4,915,630 A * | 4/1990 | Honig | A61C 5/007 433/215 |
| 4,935,635 A | 6/1990 | O'Harra | |
| 4,936,862 A | 6/1990 | Walker et al. | |
| 4,937,928 A | 7/1990 | Van Der Zel | |
| 4,941,826 A | 7/1990 | Loran et al. | |
| 4,964,770 A | 10/1990 | Steinbichler et al. | |
| 4,975,052 A | 12/1990 | Spencer et al. | |
| 4,983,334 A | 1/1991 | Adell | |
| 5,011,405 A | 4/1991 | Lemchen | |
| 5,017,133 A | 5/1991 | Miura | |
| 5,027,281 A | 6/1991 | Rekow et al. | |
| 5,035,613 A | 7/1991 | Breads et al. | |
| 5,055,039 A * | 10/1991 | Abbatte | A61C 7/146 433/24 |
| 5,059,118 A | 10/1991 | Breads et al. | |
| 5,100,316 A | 3/1992 | Wildman | |
| 5,121,333 A | 6/1992 | Riley et al. | |
| 5,125,832 A | 6/1992 | Kesling | |
| 5,128,870 A | 7/1992 | Erdman et al. | |
| 5,130,064 A | 7/1992 | Smalley et al. | |
| 5,131,843 A | 7/1992 | Hilgers et al. | |
| 5,131,844 A | 7/1992 | Marinaccio et al. | |
| 5,139,419 A | 8/1992 | Andreiko et al. | |
| 5,145,364 A | 9/1992 | Martz et al. | |
| 5,176,517 A | 1/1993 | Truax | |
| 5,184,306 A | 2/1993 | Erdman et al. | |
| 5,186,623 A | 2/1993 | Breads et al. | |
| 5,257,203 A | 10/1993 | Riley et al. | |
| 5,273,429 A | 12/1993 | Rekow et al. | |
| 5,278,756 A | 1/1994 | Lemchen et al. | |
| 5,328,362 A | 7/1994 | Watson et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,440,326 A | 8/1995 | Quinn | |
| 5,440,496 A | 8/1995 | Andersson et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,456,600 A | 10/1995 | Andreiko et al. | |
| 5,474,448 A | 12/1995 | Andreiko et al. | |
| RE35,169 E | 3/1996 | Lemchen et al. | |
| 5,518,397 A | 5/1996 | Andreiko et al. | |
| 5,528,735 A | 6/1996 | Strasnick et al. | |
| 5,533,895 A | 7/1996 | Andreiko et al. | |
| 5,542,842 A | 8/1996 | Andreiko et al. | |
| 5,549,476 A | 8/1996 | Stern | |
| 5,562,448 A | 10/1996 | Mushabac | |
| 5,587,912 A | 12/1996 | Andersson et al. | |
| 5,605,459 A | 2/1997 | Kuroda et al. | |
| 5,607,305 A | 3/1997 | Andersson et al. | |
| 5,614,075 A | 3/1997 | Andre, Sr. | |
| 5,621,648 A | 4/1997 | Crump | |
| 5,645,420 A | 7/1997 | Bergersen | |
| 5,645,421 A | 7/1997 | Slootsky | |
| 5,655,653 A | 8/1997 | Chester | |
| 5,683,243 A | 11/1997 | Andreiko et al. | |
| 5,683,244 A | 11/1997 | Truax | |
| 5,692,894 A | 12/1997 | Schwartz et al. | |
| 5,725,376 A | 3/1998 | Poirier | |
| 5,725,378 A | 3/1998 | Wang | |
| 5,733,126 A | 3/1998 | Andersson et al. | |
| 5,740,267 A | 4/1998 | Echerer et al. | |
| 5,742,700 A | 4/1998 | Yoon et al. | |
| 5,795,150 A * | 8/1998 | Boyd | A61F 5/566 128/861 |
| 5,799,100 A | 8/1998 | Clarke et al. | |
| 5,800,174 A | 9/1998 | Andersson | |
| 5,823,778 A | 10/1998 | Schmitt et al. | |
| 5,848,115 A | 12/1998 | Little et al. | |
| 5,857,853 A | 1/1999 | Van Nifterick et al. | |
| 5,866,058 A | 2/1999 | Batchelder et al. | |
| 5,879,158 A | 3/1999 | Doyle et al. | |
| 5,880,961 A | 3/1999 | Crump | |
| 5,880,962 A | 3/1999 | Andersson et al. | |
| 5,885,073 A * | 3/1999 | Kussick | A61C 7/08 128/848 |
| 5,934,288 A | 8/1999 | Avila et al. | |
| 5,957,686 A * | 9/1999 | Anthony | A61C 7/00 433/19 |
| 5,964,587 A | 10/1999 | Sato | |
| 5,971,754 A | 10/1999 | Sondhi et al. | |
| 5,975,893 A | 11/1999 | Chishti et al. | |
| 6,015,289 A | 1/2000 | Andreiko et al. | |
| 6,044,309 A | 3/2000 | Honda | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,123,544 A | 9/2000 | Cleary | |
| 6,152,731 A | 11/2000 | Jordan et al. | |
| 6,183,248 B1 | 2/2001 | Chishti et al. | |
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,244,861 B1 | 6/2001 | Andreiko et al. | |

(56) References Cited

U.S. PATENT DOCUMENTS

| | | | |
|---|---|---|---|
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,364,659 B1* | 4/2002 | Lotte | A61C 7/00 433/18 |
| 6,382,975 B1 | 5/2002 | Poirier | |
| 6,398,548 B1 | 6/2002 | Muhammad et al. | |
| 6,402,707 B1 | 6/2002 | Ernst | |
| 6,464,495 B1* | 10/2002 | Voudouris | A61C 7/00 433/18 |
| 6,482,298 B1 | 11/2002 | Bhatnagar | |
| 6,524,101 B1 | 2/2003 | Phan et al. | |
| 6,554,611 B2 | 4/2003 | Shishti et al. | |
| 6,572,372 B1* | 6/2003 | Phan | A61C 7/00 433/18 |
| 6,604,527 B1 | 7/2003 | Palmisano | |
| 6,629,840 B2 | 10/2003 | Chishti et al. | |
| 6,666,212 B2* | 12/2003 | Boyd, Sr. | A61C 7/36 128/859 |
| 6,705,863 B2 | 3/2004 | Phan et al. | |
| 6,722,880 B2 | 4/2004 | Chishti et al. | |
| 7,226,287 B2 | 6/2007 | Abels et al. | |
| 7,234,467 B2* | 6/2007 | Ball | A61F 5/566 128/848 |
| 7,293,987 B2* | 11/2007 | Abels | A61C 7/36 433/18 |
| 7,730,891 B2* | 6/2010 | Lamberg | A61F 5/566 128/848 |
| 8,297,286 B2* | 10/2012 | Smernoff | A61C 9/0006 128/846 |
| 8,573,224 B2* | 11/2013 | Thornton | A61F 5/566 128/848 |
| 2002/0006597 A1 | 1/2002 | Andreiko et al. | |
| 2003/0009252 A1 | 1/2003 | Pavlovskaia et al. | |
| 2003/0139834 A1 | 7/2003 | Nikolskiy et al. | |
| 2003/0207224 A1 | 11/2003 | Lotte | |
| 2003/0224311 A1 | 12/2003 | Cronauer | |
| 2003/0224314 A1 | 12/2003 | Bergersen | |
| 2004/0058295 A1* | 3/2004 | Bergersen | A61C 7/08 433/6 |
| 2004/0128010 A1 | 7/2004 | Pavlovskaia et al. | |
| 2005/0055118 A1 | 3/2005 | Nikolskiy et al. | |
| 2005/0244781 A1* | 11/2005 | Abels | A61C 7/143 433/24 |
| 2006/0014117 A1* | 1/2006 | Abels | A61C 7/36 433/18 |
| 2006/0078840 A1 | 4/2006 | Robson | |
| 2006/0099546 A1* | 5/2006 | Bergersen | A61C 7/08 433/6 |
| 2008/0102414 A1* | 5/2008 | Abels | A61C 7/00 433/19 |
| 2008/0294405 A1 | 11/2008 | Kitching et al. | |
| 2011/0005527 A1 | 1/2011 | Andrew et al. | |
| 2015/0079531 A1 | 3/2015 | Heine | |

FOREIGN PATENT DOCUMENTS

| | | |
|---|---|---|
| AU | 5598894 A | 6/1994 |
| CA | 1121955 A | 4/1982 |
| CN | 103340690 A | 10/2013 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| JP | 2008178727 A | 8/2008 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | 0001317 A1 | 1/2000 |
| WO | 2001070126 | 9/2001 |
| WO | 2006052414 A2 | 5/2006 |
| WO | 2008102132 A1 | 8/2008 |
| WO | 2012140021 | 10/2012 |
| WO | 2013139467 A1 | 9/2013 |
| WO | WO-2015020293 A1 | 2/2015 |

OTHER PUBLICATIONS

Leonardo Tavares Camardella, et al. Use of a Bite Ramp in Orthodontic Treatment. Apresentado no A.A.O.—Scientific Posterboards Exhibit No. 41-7 de maio de 2006. http://www.cleber.com.br/leonardo/.

International Search Report and Written Opinion from related PCT Application PCT/IB2015/000214 dated Sep. 1, 2015, 22 pp.

Bite Ramps, Align Orthodontics, http://www.alignortho.com/Portals/0/pdf/BITE%20RAMPS.pdf, May 3, 2012, 1 page.

Dr. Jonathan Nicozisis, Techniques for Deep Bite Correction with Invisalign, Clinical Tips & Techniques, http://www.princetonorthodontics.net/Portals/0/Nicozisis_DeepBiteCorrection_Invisalign_new0628.pdf, Jun. 2012, 4 pages.

Dr. William V. Gierie, Techniques for Deep Bite Correction with Invisalign Virtual Bite Ramps. Clinical Tips & Techniques, Jun. 2012, 2 pages.

International Search Report and Written Opinion from related PCT Application No. PCT/IB2015/002134, dated Jun. 1, 2016, 19 pp.

AADR. American Association for Dental Research, Summary of Activities, Mar. 20-23, 1980, Los Angeles, CA, p. 195.

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs,"

(56) References Cited

OTHER PUBLICATIONS an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty, NATO Symposium on Applications of Human Biostereometrics," Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy.swin.edu.au/-pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979).

Cardinal Industrial Finishes, Powder Coatings information posted at<http://www.cardinalpaint.com> on Aug. 25, 2000, 2 pages.

Carnaghan, "An Alternative to Holograms for the Portrayal of Human Teeth," 4th Int'l Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, A Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Cottingham, (1969). Gnathologic Clear Plastic Positioner, Am. J. Orthod, vol. 55, pp. 23-31.

Crawford, "CAD/CAM in the Dental Office: Does It Work?", Canadian Dental Journal, vol. 57, No. 2, pp. 121-123 (Feb. 1991).

Crawford, "Computers in Dentistry: Part 1 CAD/CAM: The Computer Moves Chairside, "Part 2 F. Duret—A Man with a Vision, Part 3 The Computer Gives New Vision—Literally," Part 4 Bytes 'N Bites—The Computer Moves from the Front Desk to the Operatory," Canadian Dental Journal, vol. 54 (9), pp. 661-666 (1988).

Crooks, "CAD/CAM Comes to USC," USC Dentistry, pp. 14-17 (Spring 1990).

Cureton, Correcting Malaligned Mandibular Incisors with Removable Retainers, J. Clin. Orthod, vol. 30, No. 7 (1996) pp. 390-395.

Curry et al., "Integrated Three-Dimensional Craniofacial Mapping at the Craniofacial Research Instrumentation Laboratory/University of the Pacific," Semin. Orthod., 7(4):258-265 (Dec. 2001).

Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC Production AG, pp. 1-7 (Jan. 1992.

Definition for gingiva. Dictionary.com p. 1-3. Retrieved from the internet Nov. 5, 2004<http://reference.com/search/search?q=gingiva>.

Defranco et al., "Three-Dimensional Large Displacement Analysis of Orthodontic Appliances," J. Biomechanics, 9:793-801 (1976).

Dental Institute University of Zurich Switzerland, Program for International Symposium JD on Computer Restorations: State of the Art of the CEREC-Method, May 1991, 2 pages total.

Dentrac Corporation, Dentrac document, pp. 4-13 (1992).

Dent-X posted on Sep. 24, 2098 at< http://www.dent-x.com/DentSim.htm>, 6 pages.

Doyle, "Digital Dentistry," Computer Graphics World, pp. 50-52, 54 (Oct. 2000).

DuraClearTM product information, Allesee Orthodontic Appliances—Pro Lab, 1 page (1997).

Duret et al., "CAD/CAM Imaging in Dentistry," Curr. Opin. Dent., 1:150-154 (1991).

Duret et al, "CAD-CAM in Dentistry," J. Am. Dent. Assoc. 117:715-720 (Nov. 1988).

Duret, "The Dental CAD/CAM, General Description of the Project," Hennson International Product Brochure, 18 pages total, Jan. 1986.

Duret,"Vers Une Prosthese Informatisee," (English translation attached), Tonus, vol. 75, pp. 55-57 (Nov. 15, 1985).

Economides, "The Microcomputer in the Orthodontic Office," JCO, pp. 767-772 (Nov. 1979).

Elsasser, Some Observations on the History and Uses of the Kesling Positioner, Am. J. Orthod. (1950) 36:368-374.

English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987).

Friede et al., "Accuracy of Cephalometric Prediction in Orthognathic Surgery," Abstract of Papers, J. Dent. Res., 70:754-760 (1987).

Futterling et a/., "Automated Finite Element Modeling of a Human Mandible with Dental Implants," JS WSCG '98 —Conference Program, retrieved from the Internet:<http://wscg.zcu.cz/wscg98/papers98/Strasser 98.pdf>, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001).

Gim-Alldent Deutschland, "Das DUX System: Die Technik," 2 pages total (2002).

Gottleib et al., "JCO Interviews Dr. James A. McNamura, Jr., on the Frankel Appliance: Part 2: Clinical 1-1 Management," J. Clin. Orthod., 16(6):390-407 (Jun. 1982).

Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).

Guess et al., "Computer Treatment Estimates in Orthodontics and Orthognathic Surgery," JCO, pp. 262-28 (Apr. 1989).

(56) References Cited

OTHER PUBLICATIONS

Heaven et a/., "Computer-Based Image Analysis of Artificial Root Surface Caries, Abstracts of Papers," J. Dent. Res., 70:528 (Apr. 17-21, 1991).

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.

Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances—Pro Lab, 1 page 1998).

JCO Interviews, Craig Andreiko , DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46 (Jan. 1978).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling, Coordinating the Predetermined Pattern and Tooth Positioner with Conventional Treatment, KN Am. J. Orthod. Oral Surg. (1946) 32:285-293.

Kesling et al., The Philosophy of the Tooth Positioning Appliance, American Journal of Orthodontics and Oral surgery. 1945; 31:297-304.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984). KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989).

McNamara et al., "Invisible Retainers," J. Cfin. Orthod., pp. 570-578 (Aug. 1985).

McNamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).

Mormann et al., "Marginale Adaptation von adhasuven Porzellaninlays in vitro," Separatdruck aus: Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," Dentist, 3 pages total, Jan./Feb. 1989.

Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).

PROCERA Research Projects, "PROCERA Research Projects 1993—Abstract Collection," pp. 3-7; 28 (1993).

Proffit et al., Contemporary Orthodontics, (Second Ed.), Chapter 15, Mosby Inc., pp. 470-533 (Oct. 1993.

Raintree Essix & ARS Materials, Inc., Raintree Essix, Technical Magazine Table of contents and Essix Appliances,< http:// www. essix.com/magazine/defaulthtml> Aug. 13, 1997.

Redmond et al., "Clinical Implications of Digital Orthodontics," Am. J. Orthod. Dentofacial Orthop., 117(2):240-242 (2000).

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

Rekow, "Dental CAD-CAM Systems: What is the State of the Art?", J. Amer. Dent. Assoc., 122:43-48 1991.

Rekow et al., "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

(56) References Cited

OTHER PUBLICATIONS

Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients,<http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98 —Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances—Pro Lab product information for patients, 2 pages (2002).

* cited by examiner

TREATMENT PLAN SPECIFIC BITE ADJUSTMENT STRUCTURES

BACKGROUND

The present disclosure is related generally to the field of dental treatment. More particularly, the present disclosure is related to systems, methods, computing device readable media, and devices for treatment plan specific bite adjustment structures.

Dental treatments may involve, for instance, restorative and/or orthodontic procedures. Restorative procedures may be designed to implant a dental prosthesis (e.g., a crown, bridge inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth over a period of time.

As an example, orthodontic repositioning may be provided through a dental process that uses positioning appliances for realigning teeth. Such appliances may utilize a thin shell of material having resilient properties, referred to as an "aligner," that generally conforms to a user's teeth but is slightly out of alignment with a current tooth configuration.

Placement of such an appliance over the teeth may provide controlled forces in specific locations to gradually move the teeth into a new configuration. Repetition of this process with successive appliances in progressive configurations can move the teeth through a series of intermediate arrangements to a final desired arrangement.

Such systems typically utilize materials that are light weight and/or transparent to provide as a set of appliances that can be used serially such that as the teeth move, a new appliance can be implemented to further move the teeth.

In various instances, a patient may have a malocclusion, where the patient's teeth do not line up properly. One example of a malocclusion is a deep bite, which is an acute case of an overbite where the patient's lower teeth are overlapped by the upper teeth and the lower incisors come into contact with the gingival tissue in the upper arch of the jaw. A deep bite can be an aesthetic problem and/or a problem with health consequences such as damage to the roots of the upper teeth, damage to the gingival tissue in the upper arch of the jaw, and/or wearing of the bottom teeth from frictional contact with the upper teeth, among others.

Some previous approaches to correcting a deep bite condition in a patient may include intrusion of the anterior (e.g., incisors and/or canines) teeth and/or extrusion of the posterior teeth (e.g., premolars and/or molars). Extrusion of the posterior teeth may be facilitated by the use of bite turbos (e.g., metal blocks adhered to a back (lingual) surface of the upper anterior teeth to reduce contact between posterior teeth in opposing jaws and allow for more eruption), anterior bite plates contacting the anterior dentition while allowing posterior eruption (e.g., in non-adult patients), twin blocks (e.g., blocks with an inclined occlusal plane are placed one on an upper dentition and one on a lower dentition to reduce contact between posterior teeth), among others. However, extrusion of posterior teeth in adult patients may lead to unstable results. Intrusion of the anterior teeth may be facilitated by anchor bend (e.g., metal anchors on the molars that are used to apply an upward force to the incisors), J-hook headgear, expansion screws, bypass archwires that bypass premolars and/or canines to maintain reduced forces by lengthening the span between molars and incisors, among others. Another previous approach to correcting a deep bite condition in a patient may be orthognathic surgical correction.

DETAILED DESCRIPTION

Figure 1:
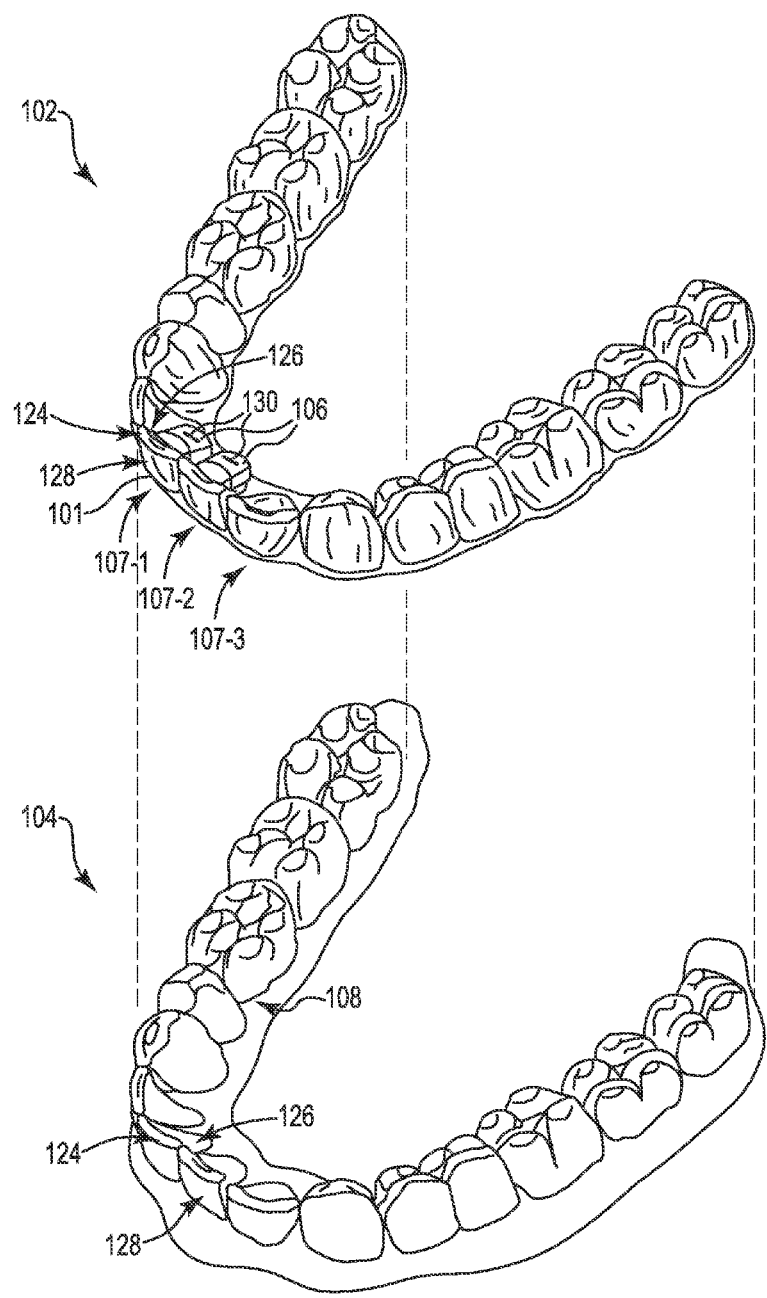
FIG. 1 illustrates a perspective view of a dental position adjustment appliance including a number of bite adjustment structures being applied to a set of teeth according to one or more embodiments of the present disclosure.

In contrast to some previous approaches, a number of embodiments of the present disclosure feature a dental positioning appliance (e.g., aligner) including a number of bite adjustment structures positioned thereon in a treatment specific fashion. For example, the bite adjustment structures can be placed according to a stage of treatment associated with the appliance. One, several, or all of a series of appliances can include bite adjustment structures that are positioned (e.g., with a shape and location) that is specific to a respective stage of a treatment plan associated with each appliance. In some embodiments, the bite adjustment structures can be formed of a same material as the appliance and/or formed at a same time as the appliance.

In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice the embodiments of this disclosure, and it is to be understood that other embodiments may be utilized and that process and/or structural changes may be made without departing from the scope of the present disclosure. As used herein, "a number of" a particular thing can refer to one or more of such things (e.g., a number of bite adjustment structures can refer to one or more bite adjustment structures).

The figures herein follow a numbering convention in which the first digit or digits correspond to the drawing figure number and the remaining digits identify an element or component in the drawing. Similar elements or components between different figures may be identified by the use of similar digits. For example, 106 may reference element "06" in FIG. 1, and a similar element may be referenced as 606 in FIG. 6. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention, and should not be taken in a limiting sense.

FIG. 1 illustrates a perspective view of a dental position adjustment appliance 102 including a number of bite adjustment structures 106 being applied to a set of teeth 104 according to one or more embodiments of the present disclosure. Appliances according to the present disclosure can include, in some embodiments, a plurality of incremental dental position adjustment appliances. The appliances, such as appliance 102 illustrated in FIG. 1, can be utilized to incrementally implement a treatment plan such as by affecting incremental repositioning of individual teeth in the jaw, among other suitable uses. Appliances, such as appliance 102, can be fabricated according to a virtual dental model that has had positions of a number of teeth adjusted according to one or more embodiments of the present disclosure.

Appliances can include any positioners, retainers, and/or other removable appliances for finishing and maintaining teeth positioning in connection with a dental treatment. These appliances may be utilized by the treatment professional in performing a treatment plan. For example, a treatment plan can include the use of a set of appliances, created according to models described herein.

An appliance (e.g., appliance 102 in FIG. 1) can, for example, be fabricated from a polymeric shell, and/or formed from other material, having a plurality of cavities therein (e.g., cavity 107-1, cavity 107-2, generally referred to herein as cavities 107). The cavities 107 can be designed (e.g., shaped) to receive one or more teeth 104 and/or apply force to reposition one or more teeth 104 of a jaw from one teeth arrangement to a successive teeth arrangement. The shell may be designed to fit over a number of, or in many instances all, teeth 104 present in the upper and/or lower jaw.

The appliance 102 can include a number of bite adjustment structures 106 formed of a same material as the shell. In some embodiments, the bite adjustment structures 106 can be formed of the same material as the shell as a continuous body. The bite adjustment structures 106 can be formed at a same time as the shell (e.g., from a same bulk material), such as during a vacuum forming process, where the material is vacuum formed over a model of teeth that is formed based on data representing a user's teeth.

The shell can include cavities 107 (e.g., where each cavity 107 corresponds to a tooth). The bite adjustment structures 106 can be a part of a cavity 107. A cavity, such as cavity 107-3, that does not include a bite adjustment structure 106 can be shaped to mate with a particular tooth. For example, cavity 107-3 can be shaped to mate with three surfaces of a corresponding tooth to be received therein. The three surfaces can be a front (facial) surface 128, a back (lingual) surface 126, and a biting (incisal) surface 124. The cavity 107-3 may be slightly out of alignment with a current configuration of the particular tooth (e.g., to facilitate aligning the particular tooth to a desired configuration), but the cavity 107-3 can generally conform to the shape of the particular tooth such that there is not much space between the cavity 107-3 and the particular tooth when the appliance 102 is worn.

Figure 7A:
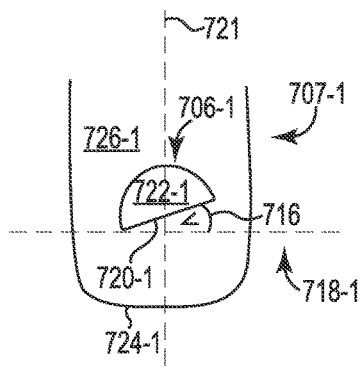
FIG. 7A illustrates a cross-section taken along cut line 7A-7A of a portion of the appliance illustrated in FIG. 6 according to a number of embodiments of the present disclosure.
Figure 7B:
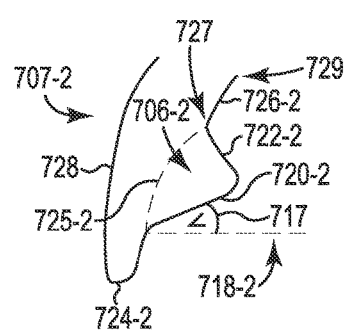
FIG. 7B illustrates a cross-section taken along cut line 7B-7B of a portion of the appliance illustrated in FIG. 6 according to a number of embodiments of the present disclosure.
Figure 7C:
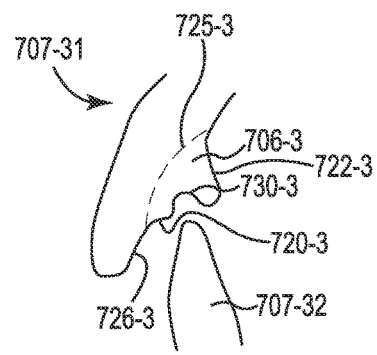
FIG. 7C illustrates a cross-section analogous to the cross-section illustrated in FIG. 7B of a portion of a first appliance and a second appliance according to a number of embodiments of the present disclosure.

In contrast, a cavity, such as cavity 107-1, that includes a bite adjustment structure 106 can be shaped to mate with two surfaces of a particular tooth. For an incisor or canine, the two surfaces can be a front (facial) surface 128 and a biting (incisal) surface 124. The back surface (lingual) surface 126 of the cavity 107-1 can include the bite adjustment structure 106 extending therefrom. The bite adjustment structure 106 can form a part of the cavity 107-1 such that when worn over a particular tooth, space exists between the tooth and the bite adjustment structure 106. FIGS. 7B and 7C illustrate this space in more detail.

The bite adjustment structures 106 can extend from the appliance 102 toward the back of the mouth (in a facial-lingual direction) and be designed to interface with teeth of the jaw opposing the jaw over which the appliance 102 is intended to be worn. For example, the appliance 102 can be designed to fit over teeth in a user's upper jaw and the bite adjustment structures 106 can be designed to interface with teeth of the user's lower jaw. The shape (e.g., size and/or contours, angle(s), etc.) and location (e.g., position on the cavity) of each of the bite adjustment structures 106 can be specific to a stage of a treatment plan for which the appliance 102 was designed. For example, successive appliances created according to a treatment plan may have differently shaped and/or located bite adjustment structures 106. A particular bite adjustment structure 106 can have a shape and location specific to a particular stage of the treatment plan based on at least one of an interface with a particular tooth of an opposing jaw, an intended use, and an orientation of a tooth over which the bite adjustment structure 106 is positioned. Bite adjustment structures 106 that have shapes and locations specific to particular stages of treatment can be advantageous over some previous approaches that use generic and/or uniform attachments that are not specific to treatment stages and therefore may not accurately provide the desired correction for the treatment stage during which they are used. Such inaccurate treatment can lead to lengthening treatment plans, a need for a revised treatment plan, and/or unnecessary user discomfort, among other drawbacks. In contrast a number of embodiments of the present disclosure allow for more timely, accurate, and/or comfortable execution of treatment plans.

In some embodiments, an edge 101 of a cavity 107 opposite the biting (incisal) surface 124 of the cavity 107 can be shaped to extend beyond a gingival line 108 of the user. Extending portions of the shell over the gingival line 108 of the jaw can help to distribute a counterforce (e.g., counter to a number of forces applied to the bite adjustment structures 106) to other portions of the jaw.

Although not specifically illustrated, in some embodiments, for a particular stage in a treatment plan, both an upper appliance (an appliance designed to fit over teeth of a user's upper jaw) and lower appliance (an appliance designed to fit over teeth of a user's lower jaw) can include a number of bite adjustment structures. A particular stage in a treatment plan can include bite adjustment structures on only one of an upper appliance and a lower appliance. A particular stage in a treatment plan may not include any bite adjustment structures on either an upper appliance or a lower appliance. A particular stage in a treatment plan can include bite adjustment structures on cavities corresponding to incisors, canines, premolars, and/or molars, and/or any combination thereof.

Bite adjustment structures on the upper appliance can be designed to interface with teeth of the lower jaw and the bite adjustment structures on the lower appliance can be designed to interface with teeth of the upper jaw. As used herein, a bite adjustment structure being "designed to interface with teeth of an opposing jaw" can mean that the bite adjustment structure is designed to interface with teeth of an opposing jaw that are or are not covered by another appliance. In some embodiments, a bite adjustment structure on a cavity of a first appliance can be designed to interface with a corresponding providing structure on a cavity of a second appliance over an opposing jaw (e.g., as illustrated and described with respect to FIG. 7D).

An upper appliance can include a number of bite adjustment structures 106 on a back (e.g., lingual) side of cavities 107 designed to receive upper anterior teeth. The number of bite adjustment structures 106 can interface with lower anterior teeth and receive an inherent force therefrom when a user bites (e.g., so as to provide a disocclusion between posterior teeth of the user). In some embodiments, the appliance 102 can be designed to selectively distribute a counterforce (counter to an inherent force generated by the user's biting) to the posterior upper dentition.

The bite adjustment structures 106 can be designed to provide a disocclusion between opposing jaws. Providing a disocclusion between opposing jaws can allow for adjustment (e.g., correction) a vertical relationship between the upper and lower jaws. That is, the bite adjustment structures 106 can be designed and intended for adjustment of the vertical relationship between upper and lower jaws and/or a vertical relationship between respective teeth in the upper and lower jaws. In some embodiments, the appliance 102 can be designed to reposition a number of teeth 104 over which the appliance 102 is worn while the bite adjustment structures 106 provide a disocclusion between opposing jaws. Providing a disocclusion between opposing jaws can help prevent appliances on opposing jaws from interacting (e.g., touching, allowing interaction of forces, etc.) with each other (e.g., except at the bite adjustment structures 106). Providing a disocclusion between opposing jaws can adjust an occlusal plane (e.g., a global occlusal plane) of the user. Such an adjustment can be temporary (e.g., while the appliance 102 is worn) and/or more permanent (e.g., by allowing for extrusion of teeth such as molars). For example, the bite adjustment structures 106 can be designed to provide a disocclusion between opposing posterior teeth when the user bites (e.g., in some instances, a number of anterior teeth of the user may contact a bite adjustment structure 106 on an appliance worn over an opposing jaw, which can prevent the user's posterior teeth from occluding). As used herein, "disocclusion" includes the provision of space between corresponding teeth of opposing jaws so that the teeth do not bind with and/or contact each other.

Figure 2:
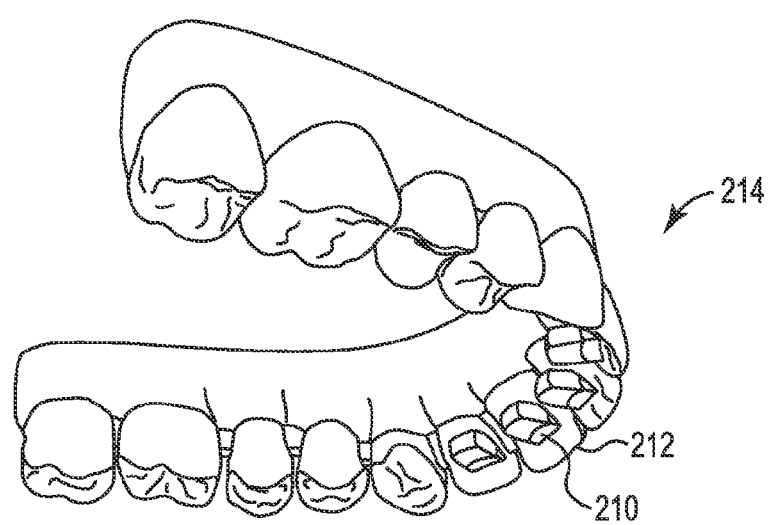
FIG. 2 illustrates a perspective view of a digital model of a jaw including a number of bite adjustment structures positioned on incisors according to a number of embodiments of the present disclosure.

FIG. 2 illustrates a perspective view of a digital model 214 of a jaw including a number of bite adjustment structures 210 positioned on incisors according to a number of embodiments of the present disclosure. A number of embodiments of the present disclosure include instructions that are executable by a processor (e.g., software), which can be fixed in a non-transitory computing device readable medium, to model a user's jaws (e.g., including teeth, roots, gingiva, and/or supporting structure, etc.). The instructions can be executed to create and/or modify a treatment plan to incrementally adjust the user's teeth and/or bite, among other adjustments, via application of a series of appliances as described herein. The instructions can be executed to provide modified models of the user's jaws for each of the various stages of the treatment plan for fabrication (e.g., via rapid prototyping such as stereolithography) of physical models corresponding to the digital models 214. The physical models can be used for the fabrication (e.g., via thermoforming) of appliances thereover.

According to a number of embodiments of the present disclosure, the instructions can be executed to position a number of digital bite adjustment structures 210 on a corresponding number of digital teeth 212 of a digital model 214 of a jaw. The instructions can be executed to position the digital bite adjustment structures 210 on the digital teeth of the digital model 214 of the jaw at a particular stage of treatment and/or adjust a position of the digital bite adjustment structures 210 for subsequent stages of treatment. The digital model 214 of the jaw can be different at each stage of treatment according to the treatment plan (e.g., positioning of the digital teeth can change). The instructions can be executed to adjust the position of the digital bite adjustment structures 210 according to changes to the digital model 214 of the jaw between treatment stages and/or according to anticipated changes in subsequent stages of treatment (e.g., to help effectuate a desired change to the digital model 214 of the jaw).

For each stage of treatment, the instructions can be executed to model forces applied to the digital model 214 of the jaw by an appliance corresponding to that stage (to simulate actual forces to be applied to a user's physical jaw by a physical appliance). Those forces can include forces applied to the digital model 214 of the jaw by virtue of the appliance being slightly out of alignment with a current configuration of the digital teeth and/or include inherent forces applied to the aligner by the user (e.g., when the user bites on the bite adjustment structures). The instructions can be executed to adjust the shape of the digital model 214 of the jaw such that a corresponding appliance formed thereover distributes a counterforce (counter to the inherent force applied by the user to the bite adjustment structures) to a number of posterior teeth of the physical jaw of the user.

Any of the number of digital models illustrated and/or described herein (e.g., FIGS. 2, 3A-3D, 4, 5, etc.) can represent a stage of a treatment plan, can be used to model forces applied to the digital models, can be used to create a physical model for formation of a physical appliance thereover, can be used for direct fabrication of a physical appliance (without creating a physical model), among other uses.

Positioning and/or adjustment of positioning of digital bite adjustment structures 210 on a digital model 214 of a jaw can be automatic (e.g., by operation of software based on force modeling for a particular stage of treatment), manual (e.g., by operation of an operator interacting with the digital model via an interface with a computing device), or a combination thereof. Likewise, the shape (e.g., size, orientation (e.g., various angles with respect to references)) and/or attachment location (on the digital teeth) of the digital bite adjustment structures 210 can be automatically set by the software, by manual operation (e.g., an operator can specify the necessary criteria of the digital bite adjustment structures 210 and/or modify default criteria provided by the software), or a combination thereof.

As described herein, the bite adjustment structures can be used to provide a disocclusion and/or adjust canine guidance, among other uses. The instructions to position the digital bite adjustment structures 210 can incorporate a result of instructions to model forces used to reposition digital teeth 212. For example, the instructions can be executed to model a first number of forces used to reposition a corresponding number of digital teeth 212 a first distance according to a first stage ("first" indicating an arbitrary stage, not necessarily an original stage) of a treatment plan and the instructions can be executed to incorporate a result of modeling the first number of forces in order to position the digital bite adjustment structures 212. The instructions executed to adjust a position of the digital bite adjustment structures 212 can incorporate a result of instructions executed to calculate a second number of forces used to reposition the number of digital teeth 212 a second distance according to a second stage of the treatment plan (e.g., a stage subsequent to the first stage, not necessarily sequential thereto).

According to a number of embodiments of the present disclosure, physical bite adjustment structures do not need to be attached to a user's physical teeth in order to fabricate appliances that include bite adjustment structures therein. With digital modeling, an impression of the user's teeth (without physical attachments) can be made and the digital bite adjustment structures 210 can be added by software. Such embodiments can be beneficial in reducing chair time for users in a professional's office and/or reduce the use of materials associated with physical attachments, which can reduce costs. Such embodiments can be beneficial in reducing user discomfort that may be associated with physical attachments, even if the physical attachments are temporary.

Figure 3A:
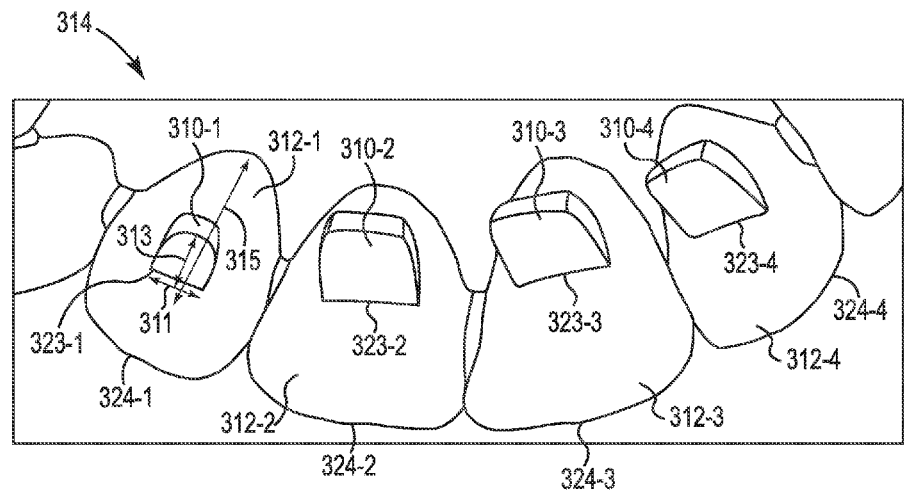
FIG. 3A illustrates a perspective view of a portion of a digital model of a jaw corresponding to a first stage of treatment including a number of digital bite adjustment structures positioned thereon according to a number of embodiments of the present disclosure.

FIG. 3A illustrates a perspective view of a portion of a digital model 314 of a jaw corresponding to a first stage of treatment including a number of digital bite adjustment structures 310 positioned thereon according to a number of embodiments of the present disclosure. The digital model 314 includes a number of digital teeth 312-1, 312-2, 312-3, 312-4 (e.g., incisors) that each include a corresponding digital bite adjustment structure 310-1, 310-2, 310-3, 310-4.

Figure 3B:
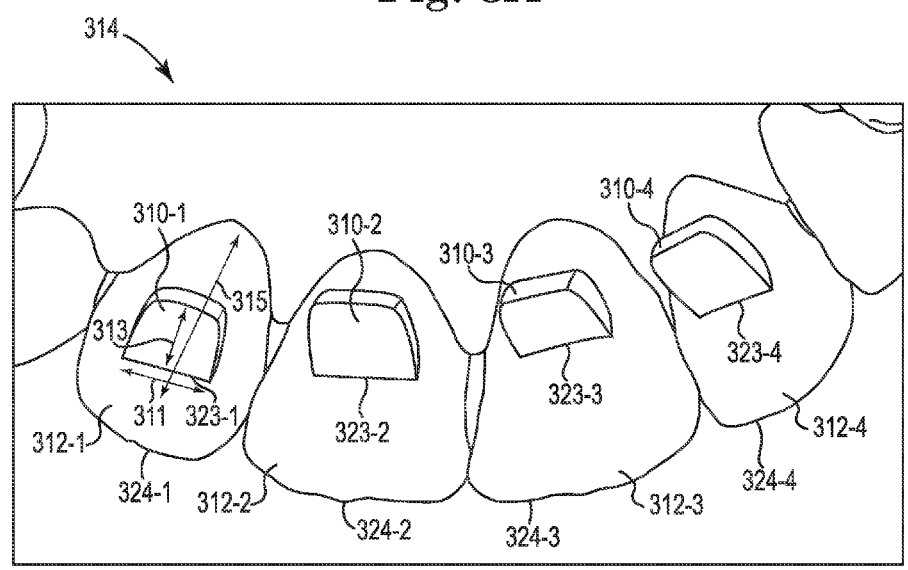
FIG. 3B illustrates a perspective view of a portion of a digital model of a jaw corresponding to a second stage of treatment including a number of digital bite adjustment structures positioned thereon according to a number of embodiments of the present disclosure.
Figure 3C:
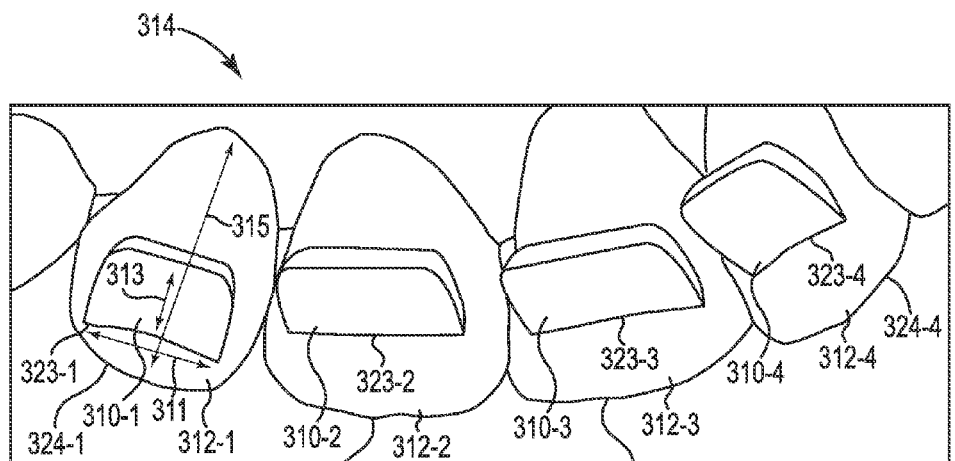
FIG. 3C illustrates a perspective view of a portion of a digital model of a jaw corresponding to a third stage of treatment including a number of digital bite adjustment structures positioned thereon according to a number of embodiments of the present disclosure.
Figure 3D:
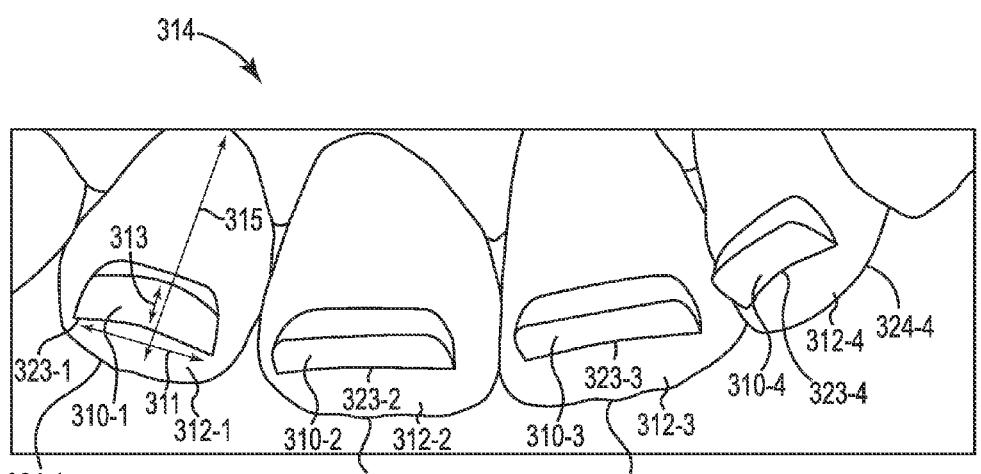
FIG. 3D illustrates a perspective view of a portion of a digital model of a jaw corresponding to a fourth stage of treatment including a number of digital bite adjustment structures positioned thereon according to a number of embodiments of the present disclosure.

FIG. 3B illustrates a perspective view of a portion of a digital model 314 of a jaw corresponding to a second stage of treatment including a number of digital bite adjustment structures 310 positioned thereon according to a number of embodiments of the present disclosure. FIG. 3C illustrates a perspective view of a portion of a digital model 314 of a jaw corresponding to a third stage of treatment including a number of digital bite adjustment structures 310 positioned thereon according to a number of embodiments of the present disclosure. FIG. 3D illustrates a perspective view of a portion of a digital model 314 of a jaw corresponding to a fourth stage of treatment including a number of digital bite adjustment structures 310 positioned thereon according to a number of embodiments of the present disclosure.

"First stage" does not necessarily mean the original stage of a treatment plan, but is a relative term with respect to other stages. For example, the "first stage" may be a second stage of a 50 stage treatment plan, while the "second stage" illustrated in FIG. 3B may be a tenth stage of the 50 stage treatment plan, while the "third stage" illustrated in FIG. 3C may be a 30th stage of the 50 stage treatment plan, and the "fourth stage" illustrated in FIG. 3D may be a 40th stage of the 50 stage treatment plan.

Embodiments can include more or fewer bite adjustment structures 310 than are illustrated in FIGS. 3A-3D. For example, some treatment plans may include four bite adjustment structures 310 for a first stage and two bite adjustment structures for a second stage. Each of the bite adjustment structures 310 can have a shape and location specific to the respective stage of the treatment plan.

FIG. 3A includes a first digital tooth 312-1 with a first digital bite adjustment structure 310-1 that is smaller than a second digital bite adjustment structure 310-2 on a second digital tooth 312-2. The first digital bite adjustment structure 310-1 is smaller than the second digital bite adjustment structure 310-2 in both a direction between adjacent teeth in the same jaw (mesial-distal direction) 311 and in a direction between the front of the mouth and the back of the mouth (facial-lingual direction) 313. In some embodiments, different bite adjustment structures can have different sizes in a direction between the root and the tip of a tooth (gingival-incisal/coronal direction) 315. The first digital bite adjustment structure 310-1 is smaller than a third digital bite adjustment structure 310-3 on a third digital tooth 312-3 and smaller than a fourth digital bite adjustment structure 310-4 on a fourth digital tooth 312-4. The third digital bite adjustment structure 310-3 is approximately the same size as the second digital bite adjustment structure 310-2. The fourth digital bite adjustment structure is smaller than the second digital bite adjustment structure 310-2 and the third digital bite adjustment structure 310-3, but larger than the first digital bite adjustment structure 310-1. Bite adjustment structures can have different angles as illustrated and described in more detail with respect to FIGS. 7A-7B.

A bite adjustment structure can be designed with a different (e.g., smaller) size, for example, as corresponding teeth of opposing jaws get closer together during treatment.

A bite adjustment structure can be designed with a different (e.g., larger) size, for example, as corresponding teeth of opposing jaws get farther apart during treatment. A bite adjustment structure can have a smaller or larger size in a direction between adjacent teeth in the same jaw (mesial-distal direction) 311 dependent upon proximity to one or more adjacent teeth (e.g., a bite adjustment structure can be designed to be smaller/larger to account for crowding/spacing so that the bite adjustment structure does not interfere with neighboring teeth).

A bite adjustment structure can be designed to be in a different location on a tooth for different stages of treatment. As illustrated between FIG. 3B and FIG. 3C, an edge 323-1 of the digital bite adjustment structure 310-1 that is closest to the biting (incisal) surface 324-1 moved closer to the biting (incisal) surface 324-1 of the digital tooth 312-1. Furthermore, the digital bite adjustment structure 310-1 increased in size in both a direction between adjacent teeth in the same jaw (mesial-distal direction) 311 and a direction between the root and the tip of a tooth (gingival-incisal/coronal direction) 315 between the second stage and the third stage. Bite adjustment structures can be designed to change location on a tooth between treatment stages based on, for example, changes in intrusion or extrusion of the tooth (or a corresponding tooth on an opposing jaw) and/or movement of the tooth (or a corresponding tooth on an opposing jaw) (e.g., movement in a direction between adjacent teeth in the same jaw (mesial-distal direction) 311). For example, if a tooth is intruded during treatment, a bite adjustment structure for that tooth may be moved toward a biting (incisal) surface of the tooth in a subsequent stage of treatment to allow a corresponding tooth on the opposing jaw to continue to make contact with the bite adjustment structure. As used herein, "intrusion" includes forcing a tooth back into a jaw and/or preventing eruption of the tooth from the jaw.

Across FIGS. 3A-3D, the edges 323-1, 323-2, 323-3, 323-4 of the digital bite adjustment structures 310-1, 310-2, 310-3, 310-4 closest to the biting (incisal) surfaces 324-1, 324-2, 324-3, 324-4 of the teeth generally change location toward the biting (incisal) surfaces 324-1, 324-2, 324-3, 324-4 of the digital teeth 312-1, 312-2, 312-3, 312-4. Such a change in location can be designed for the digital bite adjustment structures 310-1, 310-2, 310-3, 310-4, for example, as part of a treatment plan where the digital teeth 312-1, 312-2, 312-3, 312-4 are being intruded into the jaw (as the teeth move up into the jaw, an occlusal plane defined by contact with the corresponding teeth on the opposing jaw would generally move in the direction between the root and the tip of a tooth (gingival-incisal/coronal direction) 315 toward the biting (incisal) surfaces 324-1, 324-2, 324-3, 324-4 of the digital teeth 312-1, 312-2, 312-3, 312-4).

Figure 4:
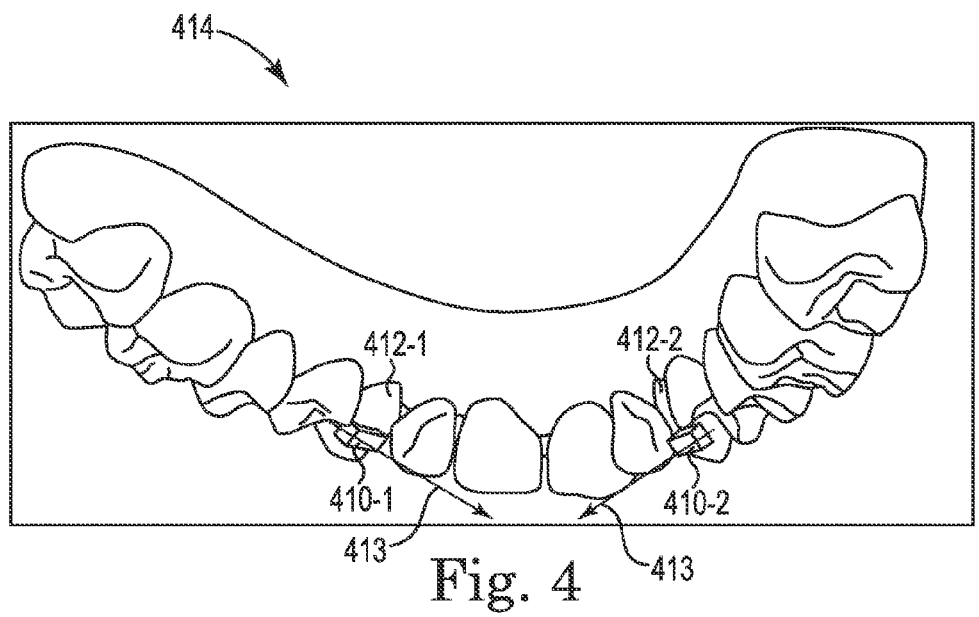
FIG. 4 illustrates a perspective view of a digital model of a jaw including a number of digital bite adjustment structures positioned on digital canines according to a number of embodiments of the present disclosure.

FIG. 4 illustrates a perspective view of a digital model 414 of a jaw including a number of digital bite adjustment structures 410-1, 410-2 positioned on digital canines 412-1, 412-2 according to a number of embodiments of the present disclosure. Appliances (e.g., formed based on digital model 414) that include bite adjustment structures on canines can be used to provide a disocclusion between various opposing teeth in a user's jaws while the appliance is worn (e.g., to allow for eruption of teeth or other treatment goals).

The digital bite adjustment structures 410 can extend from the digital canines 412 in a direction from the outside of the mouth toward an inside of the mouth (facial-lingual) direction 413. Because the digital bite adjustment structures 410 are extending from digital canines 412, the digital bite adjustment structures 410 are likely (depending on specific patient tooth geometry and alignment) to extend in a direction oblique to the occlusal plane. Although the angle of each digital bite adjustment structure can be specific to the particular digital tooth from which it extends, and patient tooth geometries and alignments will differ, digital bite adjustment structures extending from digital incisors (e.g., FIG. 2) may be more closer to being parallel to the occlusal plane, digital bite adjustment structures extending from digital molars and/or premolars (e.g., FIG. 5) may be closer to being perpendicular to the occlusal plane, and digital bite adjustment structures extending from digital canines (e.g., FIG. 4) may be closer to being oblique to the occlusal plane.

According to a number of embodiments of the present disclosure, the digital bite adjustment structures 410 can be positioned on a corresponding number of digital teeth 412 of a digital model 414 of a jaw at a particular stage of treatment. The position of the digital bite adjustment structures 410 can be adjusted for subsequent stages of treatment (e.g., to help effectuate a desired change to the digital model 414 of the jaw). For example, bite adjustment structures on cavities of an appliance over a canine can be used to adjust canine guidance. Canine guidance is a feature of the canines that helps to prevent contact of posterior teeth of opposing jaws when the lower jaw slides sideways (e.g., interaction ("guidance") of the upper and lower canines provides a disocclusion between the posterior teeth of opposing jaws when the lower jaw slides sideways with respect to the upper jaw in order to protect the posterior teeth). An appliance formed with bite adjustment structures on a canine cavity can adjust canine guidance by altering the interface between the canine cavity and a corresponding tooth on an opposing jaw so that when the jaws move sideways with respect to one another the interface between the bite adjustment structure and the opposing tooth protects the posterior teeth by providing a disocclusion (e.g., where, without the bite adjustment structure the posterior teeth may contact and/or grind against each other as the jaws move sideways with respect to one another).

Figure 5:
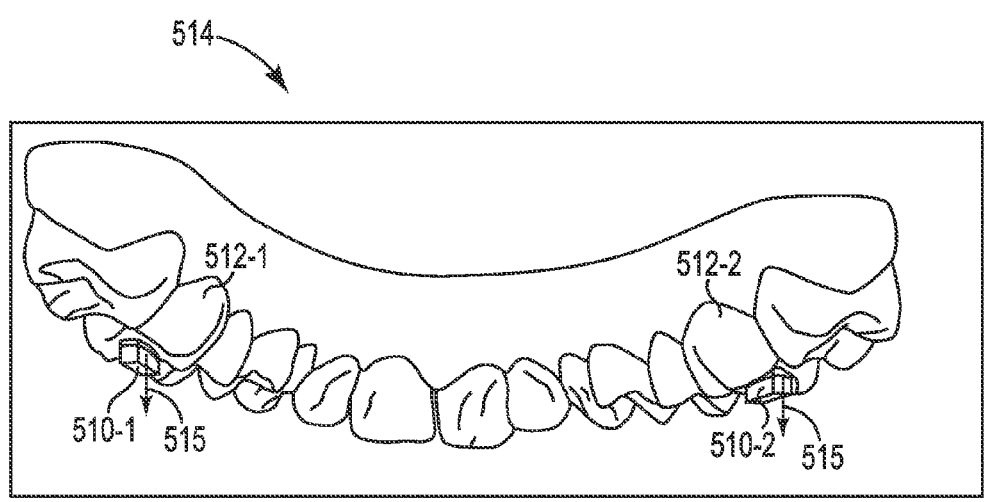
FIG. 5 illustrates a perspective view of a digital model of a jaw including a number of digital bite adjustment structures positioned on digital posterior teeth according to a number of embodiments of the present disclosure.

FIG. 5 illustrates a perspective view of a digital model 514 of a jaw including a number of digital bite adjustment structures 510-1, 510-2 positioned on digital posterior teeth 512-1, 512-2 according to a number of embodiments of the present disclosure. The digital bite adjustment structures 510 are illustrated being positioned on digital molars 512. Although not specifically illustrated, digital bite adjustment structures can be positioned on digital premolars in an analogous fashion to the digital bite adjustment structures 510 positioned on the molars 512 illustrated in FIG. 5.

The digital bite adjustment structures 510 can be positioned on a corresponding number of digital teeth 512 (e.g., posterior teeth) of a digital model 514 of a jaw at a particular stage of treatment. The position of the digital bite adjustment structures 510 can be adjusted for subsequent stages of treatment (e.g., to help effectuate a desired change to the digital model 514 of the jaw). For example, bite adjustment structures on cavities of an appliance over a molar and/or premolar can be used to provide a disocclusion between the posterior and/or anterior teeth of opposing jaws when the user bites. The digital bite adjustment structures 510 can extend from a respective cavity in a direction between the root and the tip of a tooth (gingival-incisal/coronal direction) 515. In some embodiments, the digital bite adjustment structures 510 can extend in the direction between the root and the tip of a tooth (gingival-incisal/coronal direction) 515 a distance sufficient to pass through an occlusal plane to help corresponding physical bite adjustment structures formed in an appliance based on the digital model 514 to provide a disocclusion. The disocclusion can be provided by interaction of the bite adjustment structure with teeth of the opposing jaw (e.g., the bite adjustment structure can contact a number of teeth of the opposing jaw and prevent the other teeth of the opposing jaws from contacting one another). Although not specifically illustrated, a corresponding surface of an opposite digital jaw can be contoured to receive the digital bite adjustment structure 510. An appliance formed thereover can inherit the contours so that the bite adjustment structure 510 fits nicely against the opposing appliance and avoids unwanted shifting forces.

Although not specifically illustrated, some embodiments can include a digital bite adjustment structure on a number of posterior teeth on only one side of the jaw (e.g., either left or right) for a particular stage of treatment. Including a bite adjustment structure extending from a posterior tooth on one side of the jaw can allow a number of teeth to be extruded from or erupt from an opposite side of the jaw. In some embodiments, a first stage of treatment can include a number of bite adjustment structures extending from posterior teeth on the left side of a jaw and a second stage subsequent to the first stage can include a number of bite adjustment structures extending from posterior teeth on the right side of the jaw (or vice versa). Varying the side of the jaw from which a digital bite adjustment structure extends (from a posterior tooth) can allow a number of teeth to be extruded from or erupt from both sides of the jaw alternately.

In some embodiments, a first stage of treatment can include a bite adjustment structure extending from a first posterior tooth on one side (e.g., left or right) of a jaw and a second stage subsequent to the first stage can include a bite adjustment structure extending from a second (different) posterior tooth on the same side of the jaw. Varying the tooth on the same side of the jaw from which a bite adjustment structure extends (from a posterior tooth) can allow a number of teeth to be extruded from or erupt from the same side of the jaw alternately.

Figure 6:
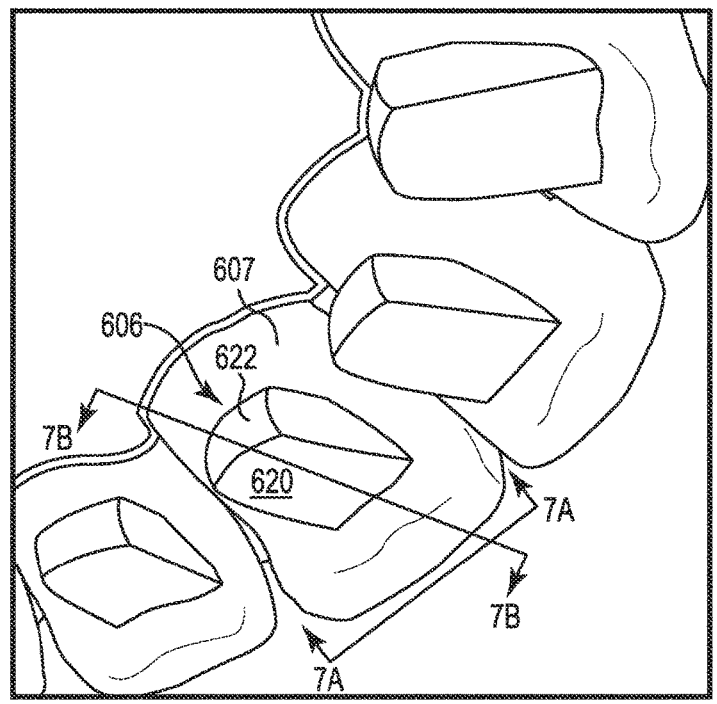
FIG. 6 illustrates a perspective view of a portion of a dental position adjustment appliance including a number of bite adjustment structures positioned thereon according to a number of embodiments of the present disclosure.
Figure 7D:
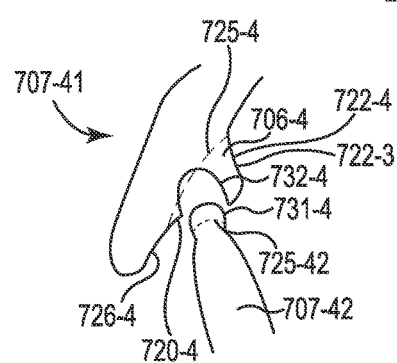
FIG. 7D illustrates a cross-section analogous to the cross-section illustrated in FIG. 7B of a portion of a first appliance and a second appliance according to a number of embodiments of the present disclosure.

FIG. 6 illustrates a perspective view of a portion of a dental position adjustment appliance including a number of bite adjustment structures 606 positioned thereon according to a number of embodiments of the present disclosure. For example, cavity 607 includes bite adjustment structure 606. Bite adjustment structure 606 includes a first surface 620 and a second surface 622. The cavity 607 that includes bite adjustment structure 606 is illustrated with cut line 7A-7A and cut line 7B-7B. FIG. 7A corresponds to cut line 7A-7A. FIGS. 7B, 7C, and 7D are different embodiments corresponding to cut line 7B-7B.

FIG. 7A illustrates a cross-section taken along cut line 7A-7A of a portion (e.g., cavity 707-1) of the appliance illustrated in FIG. 6 according to a number of embodiments of the present disclosure. The appliance includes a cavity 707-1 including a bite adjustment structure 706-1. The cavity 707-1 can be shaped to mate with two surfaces of a tooth therein when worn by a user. Note that the left and right edges of the cavity 707-1 are shown for illustrative purposes, and may not physically be part of the appliance (e.g., the appliance may have an open channel between adjacent cavities contained therein so as not to interfere with an interproximal region between adjacent teeth of a user). As described herein, bite adjustment structures can include a shape and location specific to a particular stage of a treatment plan. The bite adjustment structure 706-1 is illustrated on a back (lingual) surface 726-1 of the cavity 707-1. The cavity 707-1 (e.g., the bite adjustment structure 706-1 on the cavity 707-1) can have a first surface 720-1 extending away from a tooth within the cavity 707-1 in a front-to-back (facial-lingual) direction (out of the page) proximal to a biting (incisal) surface 724-1 of the cavity 707-1. The cavity 707-1 (e.g., the bite adjustment structure 706-1) can have a second surface 722-1 that connects with the first surface 720-1 a distance from the tooth within the cavity 707-1. The first surface 720-1 and the second surface 722-1 are both on the same side of the cavity 707-1 (e.g., the first surface 720-1 and the second surface 722-1 are both on the outside of the cavity 707-1 as opposed to the inside of the cavity 707-1 where a tooth is received). An angle 716 between the first surface 720-1 of the cavity 707-1 and an occlusal plane 718-1 of the user is illustrated.

According to a number of embodiments of the present disclosure, different cavities (not specifically illustrated in FIG. 7A) can have different angles 716 between the first surface 720-1 and the occlusal plane 718-1. Having different angles 716 between different bite adjustment structures 706-1 and the occlusal plane 718-1 can allow for more accurate modeling of forces applied to the bite adjustment structures 706-1 by opposing teeth of the user. Having different angles 716 between different bite adjustment structures 706-1 and the occlusal plane 718-1 can allow for more force to be applied to each of the bite adjustment structures 706-1 by opposing teeth of the user, for example, in a situation where a user has differently misaligned teeth in either an upper or lower jaw (e.g., where biting (incisal) surfaces 724-1 of different teeth approach the occlusal plane 718-1 with different angles). Modifying the angles 716 of individual bite adjustment structures 706-1 can allow first surfaces 720-1 (e.g., biting (incisal) surfaces) of individual bite adjustment structures 706-1 (e.g., each bite adjustment structure 706-1) to be substantially parallel to biting (incisal) surfaces of opposing teeth.

FIG. 7B illustrates a cross-section taken along cut line 7B-7B of a portion (e.g., cavity 707-2) of the appliance illustrated in FIG. 6 according to a number of embodiments of the present disclosure. With respect to FIG. 7A, FIG. 7B can illustrate the cavity 707-1 of FIG. 7A as it would appear after rotating 90 degrees about a vertical axis 721. The appliance includes a cavity 707-2 including a bite adjustment structure 706-2 according to a number of embodiments of the present disclosure. The cavity 707-2 can be shaped to mate with two surfaces of a tooth therein when worn by a user. For example, the front (facial) surface 728 of the cavity 707-2 can be shaped to mate with a front (facial) surface of a tooth therein and a biting (incisal) surface 724-2 of the cavity 707-2 can be shaped to mate with a biting (incisal) surface of a tooth therein. The back (lingual) surface 726-2 of the cavity 707-2 can be partially shaped to mate with a back (lingual) surface of a tooth therein.

The back (lingual) surface 726-2 of the cavity 707-2 is shaped to "partially mate" with a back (lingual) surface of a tooth therein, because there is a space between the tooth and the first surface 720-2 and second surface 722-2 of the bite adjustment structure 706-2 (e.g., as illustrated by the dotted line 725-2, which would otherwise represent a portion of the back (lingual) surface of the cavity 707-2). In some embodiments, the space between the tooth and the first surface 720-2 and the second surface 722-2 can be empty (e.g., hollow). In such embodiments, there is an open channel between the bite adjustment structure 706-2 and a remainder of the cavity 707-2. In some embodiments, the space between the tooth and the first surface 720-2 and the second surface 722-2 can be solid (e.g., filled with a same material as the appliance or a different material). In such embodiments, the dotted line 725-2 would appear as a solid line because it would represent a physical edge of the material filling the space between the tooth and the first surface 720-2 and the second surface 722-2.

The bite adjustment structure 706-2 is illustrated on a back (lingual) surface 726-2 of the cavity 707-2. The cavity 707-2 (e.g., the bite adjustment structure 706-2 on the cavity 707-2) can have a first surface 720-2 extending away from a tooth within the cavity 707-2 in a front-to-back (facial-lingual) direction proximal to a biting (incisal) surface 724-2 of the cavity 707-2. The cavity 707-2 (e.g., the bite adjustment structure 706-2) can have a second surface 722-2. The second surface 722-2 can extend away from a location where the back of a tooth to be received in the cavity 707-2 would be (e.g., as illustrated by dotted line 752-2). The second surface 722-2 can extend in a generally biting (incisal) direction (at least relative to the front-to-back (facial-lingual) direction in which the first surface 720-2 extends). The second surface 722-2 can depart from a point 727 where the cavity 707-2 is otherwise shaped to mate with a tooth received therein. The point 727 can be proximal to an edge 729 of the cavity 707-2 opposite the biting (incisal) surface 724-2 of the cavity 707-2. The first surface 720-2 connects with the second surface 722-2 a distance from the tooth within the cavity 707-2.

An angle 717 between the first surface 720-2 of the cavity 707-2 and an occlusal plane 718-2 of the user is illustrated. Contrasted with the angle 716 illustrated in FIG. 7A between the first surface 720-1 and the occlusal plane 718-1, which can be considered a "roll angle", the angle 717 illustrated in FIG. 7B between the first surface 720-2 and the occlusal plane 718-2 can be considered a "pitch angle." According to a number of embodiments of the present disclosure, different cavities (not specifically illustrated in FIG. 7B) can have different angles 717 between the first surface 720-2 and the occlusal plane 718-2. Having different angles 717 between different bite adjustment structures 706-2 and the occlusal plane 718-2 can allow for more accurate modeling of forces applied to the bite adjustment structures 706-2 by opposing teeth of the user. Having different angles 717 between different bite adjustment structures 706-2 and the occlusal plane 718-2 can allow for more accurate control of a direction in which force is to be applied to each of the bite adjustment structures 706-2 by opposing teeth of the user, for example, in a situation where a treatment plan for a user calls for repositioning a tooth within the cavity 707-3 in a direction other than directly toward the root and/or jaw (e.g., to correct for a tooth with improper tipping such as inclination or reclination).

FIG. 7C illustrates a cross-section analogous to the cross-section illustrated in FIG. 7B of a portion of a first appliance and a second appliance according to a number of embodiments of the present disclosure. The portion (e.g., cavity 707-31) of the first appliance includes a bite adjustment structure 706-3. The back (lingual) surface 726-3 of the cavity 707-31 can be shaped to mate partially with a back (lingual) surface of a tooth therein, because there is a space between the tooth and the first surface 720-3 and second surface 722-3 of the bite adjustment structure 706-3 (e.g., as illustrated by the dotted line 725-3, which would otherwise represent a portion of the back (lingual) surface of the cavity 707-31).

In some embodiments, the first surface 720-3 of the bite adjustment structure 706-3 can include a notch 730-3 therein positioned to receive a biting (incisal) surface of a cavity 707-32 opposite the bite adjustment structure 706-3 in an opposing jaw when the jaws of a user wearing the appliance are closed. Such a notch 730-3 can be useful in helping to control a location where an opposing cavity 707-32 contacts and/or applies force to the bite adjustment structure 706-3 so that the force applied to the bite adjustment structure is more accurately modeled in the treatment plan. Without such a notch, the opposing cavity 707-32 may slide along the first surface 720-3 of the bite adjustment structure 706-3 and apply forces to different portions of the first surface 720-3 of the bite adjustment structure 706-3, which can lead to different force vectors (e.g., different magnitudes and/or directions). More accurate modeling of the force applied to the bite adjustment structure 706-3 can lead to more favorable results from the treatment plan for the user (e.g., the actual results can more accurately reflect the modeled results in the treatment plan).

FIG. 7D illustrates a cross-section analogous to the cross-section illustrated in FIG. 7B of a portion of a first appliance and a second appliance according to a number of embodiments of the present disclosure. The portion (e.g., cavity 707-41) of the first appliance includes a bite adjustment structure 706-4. The back (lingual) surface 726-4 of the cavity 707-41 can be shaped to mate partially with a back (lingual) surface of a tooth therein, because there is a space between the tooth and the first surface 720-4 and second surface 722-4 of the bite adjustment structure 706-4 (e.g., as illustrated by the dotted line 725-4, which would otherwise represent a portion of the back (lingual) surface of the cavity 707-4).

In some embodiments, the first surface 720-4 of the bite adjustment structure 706-4 can include a receiving structure 732-4 therein positioned to receive a providing structure 731-4 of a cavity 707-42 opposite the bite adjustment structure 706-4 in an opposing jaw when the jaws of a user wearing the appliances are closed. Such a receiving structure 732-4 can be useful in helping to control a location where the opposing cavity 707-42 contacts and/or applies force to the bite adjustment structure 706-4 so that the force applied to the bite adjustment structure is more accurately modeled in the treatment plan. Without such a receiving structure, the opposing cavity 707-42 may slide along the first surface 720-4 of the bite adjustment structure 706-4 and apply forces to different portions of the first surface 720-4 of the bite adjustment structure 706-4, which can lead to different force vectors (e.g., different magnitudes and/or directions). More accurate modeling of the force applied to the bite adjustment structure 706-4 can lead to more favorable results from the treatment plan for the user (e.g., the actual results can more accurately reflect the modeled results in the treatment plan).

Figure 8:
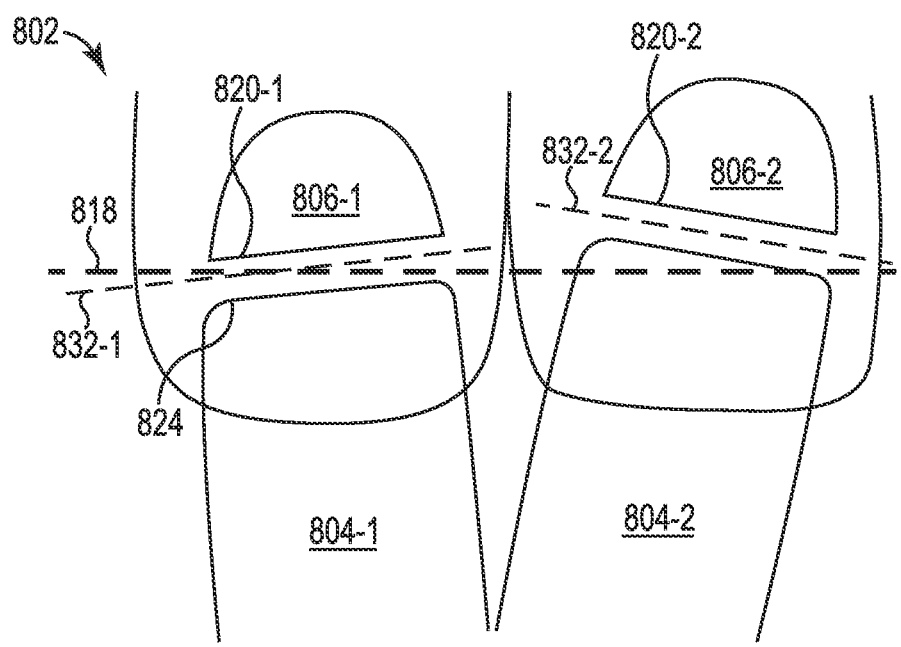
FIG. 8 illustrates an interface between a number of bite adjustment structures on a dental position adjustment appliance and a number of teeth on an opposing jaw according to a number of embodiments of the present disclosure.

FIG. 8 illustrates an interface between a number of bite adjustment structures 806-1, 806-2 on a dental position adjustment appliance 802 and a number of teeth 804-1, 804-2 on an opposing jaw according to a number of embodiments of the present disclosure. The number of teeth 804-1, 804-2 of the second jaw may or may not be covered by an appliance. The number of bite adjustment structures 806-1, 806-2 can have a shape and location specific to a particular stage of a treatment plan that the appliance 802 was designed to implement. Although only two cavities of the appliance 802 are illustrated, other cavities may be included with the appliance 802 and other cavities (some or all) can include bite adjustment structures thereon. A particular bite adjustment structure (e.g., bite adjustment structure 806-1, or more than one bite adjustment structure) can have a shape and location specific to a particular stage of the treatment plan based on at least one of an interface with a particular tooth (e.g., tooth 804-1) of the opposing jaw, an intended use, and an orientation of a tooth over which the cavity including the bite adjustment structure (e.g., bite adjustment structure 806-1) is positioned.

The interface between the bite adjustment structure 806-1 and the tooth 804-1 can be defined by a relative geometry of the first surface 820 of the bite adjustment structure 806-1 and the biting (incisal) surface 824 of the tooth 804-1 and/or a biting (incisal) surface of a cavity of an appliance thereover. The first surface 820-1 of the first cavity can be parallel to a local occlusal plane 832-1 of a tooth 804-1 opposite the first surface 820-1 of the first cavity and the first surface 820-2 of the second cavity can be parallel to a local occlusal plane 832-2 of a tooth 804-2 opposite the first surface 820-2 of the second cavity. A local occlusal plane can be an occlusal plane between a particular upper tooth and a particular lower tooth that is based only on the occlusion of the particular upper tooth and particular lower tooth (e.g., as opposed to a global occlusal plane, which is based on the occlusion of teeth in the upper and lower jaws as a whole). The first surface 820-1 of the bite adjustment structure 806-1 and/or the first surface 820-2 of the bite adjustment structure 806-2 can be designed to provide a disocclusion between opposing posterior teeth when the user bites.

Although not specifically illustrated, the teeth 804-1, 804-2 can be covered by an appliance that can include bite adjustment structures to interface with biting (incisal) surfaces of the cavities of the appliance 802. Various stages of a treatment plan can include or not include an appliance to cover the teeth 804-1, 804-2 of the opposing jaw and different stages of the treatment plan can include or not include a number of bite adjustment structures on the appliance for the opposing jaw. For example, a particular stage of a treatment plan can include an appliance over each of the upper jaw and lower jaw of a user, where each appliance includes a number of bite adjustment structures, and where the bite adjustment structures are designed to provide a disocclusion between opposing posterior teeth in order to level the teeth of the upper and lower jaws.

The positioning of the digital bite adjustment structures on the digital model can correspond to the actual position of the physical bite adjustment structures on the appliances that are fabricated according to the digital model. For example, as illustrated in FIG. 8, the bite adjustment structures 806-1, 806-2 (e.g., by operation of the user closing his jaws) may apply inherent forces 834-1, 834-2 to the teeth 804-1, 804-2 of the opposing jaw. As is also illustrated, the orientation of different teeth 804-1, 804-2 with respect to the orientation of different bite adjustment structures 806-1, 806-2 can be different based on the geometry of the interfaces between the bite adjustment structures 806-1, 806-2 and the opposing teeth 804-1, 804-2 according to a particular stage the treatment plan. Thus, the bite adjustment structures 806-1, 806-2 can be specific to individual teeth 804-1, 804-2 as well as specific to the particular stage of the treatment plan. The bite adjustment structures 806-1, 806-2 may direct an inherent force (e.g., inherent from the user biting) perpendicular to the local occlusal plane 832-1, 832-2 where the bite adjustment structures 806-1, 806-2 interact with opposing teeth 804-1, 804-2, an opposing appliance, and/or bite adjustment structures on an opposing appliance. In general there may not be lateral forces applied to the bite adjustment structures 806-1, 806-2 unless bite adjustment structures on an opposing appliance have been configured to apply such a force to the bite adjustment structures 806-1, 806-2.

Figure 9A:
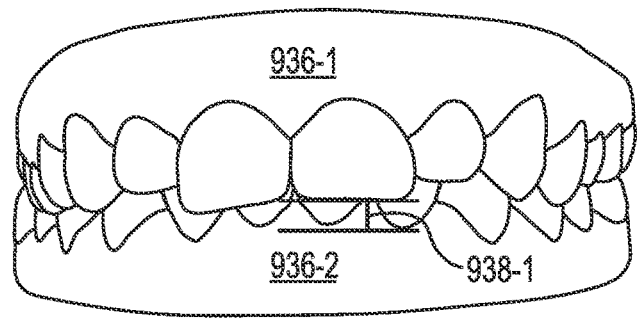
FIG. 9A illustrates jaws in a first vertical relationship according to a number of embodiments of the present disclosure.
Figure 9B:
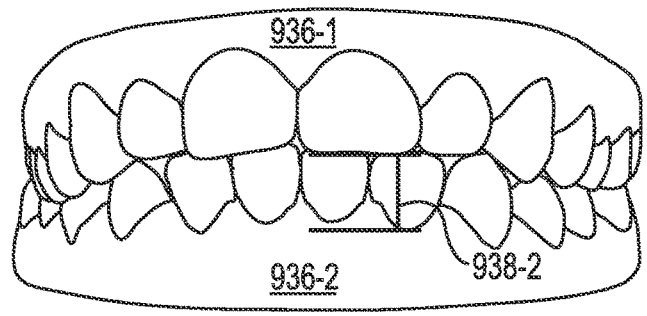
FIG. 9B illustrates jaws in a second vertical relationship according to a number of embodiments of the present disclosure.

FIG. 9A illustrates jaws 936-1, 936-2 in a first vertical relationship 938-1 according to a number of embodiments of the present disclosure. FIG. 9B illustrates jaws 936-1, 936-2 in a second vertical relationship 938-2 according to a number of embodiments of the present disclosure. In some embodiments, an appliance (e.g., including a number of bite adjustment structures) worn over the upper jaw 936-1 can be designed to adjust a vertical relationship 938-1, 938-2 between the upper jaw 936-1 and the lower jaw 936-2. As illustrated in FIG. 9A and FIG. 9B this adjustment of the vertical relationship 938-1, 938-2 can help correct for a deep bite to improve an appearance of the user's teeth and to reduce problems associated with a deep bite condition, as described herein. Embodiments are not limited to adjusting the position of the lower jaw 936-2 with respect to the upper jaw 936-1, as the position of either or both of the upper jaw 936-1 and lower jaw 936-2 can be adjusted. Furthermore, the adjustment can be performed by an appliance worn over the upper jaw 936-1 and/or an appliance worn over the lower jaw 936-2 (e.g., by interaction of a number of bite tabs on a number of appliances with a number of teeth on an opposing jaw).

Figure 10:
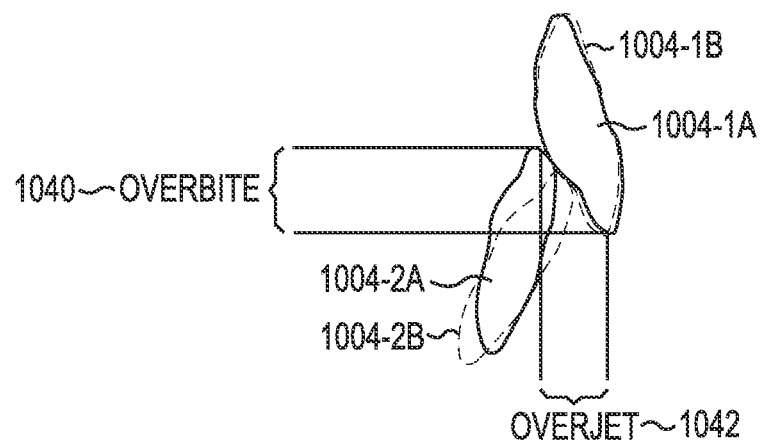
FIG. 10 illustrates a correction for overbite and overjet according to a number of embodiments of the present disclosure.

FIG. 10 illustrates a correction for overbite 1040 and overjet 1042 according to a number of embodiments of the present disclosure. Overbite 1040 can refer to a lower jaw being too far behind the upper jaw or a misalignment of the teeth. Specifically, overbite 1040 can refer to the extent of vertical (superior-inferior) overlap of the maxillary central incisors 1004-1 over the mandibular central incisors 1004-2, measured relative to the incisal ridges. Overjet 1042 can be the distance between the maxillary anterior teeth 1004-1 and the mandibular anterior teeth 1004-2 in the anterior-posterior axis. As illustrated in FIG. 10, the maxillary tooth 1004-1 can be adjusted from a first position 1004-1A to a second position 1004-1B and/or the mandibular tooth 1004-2 can be adjusted from a first position 1004-2A to a second position 1004-2B.

A number of appliances in a series of appliances created as part of a treatment plan can perform different functions. Some of the functions performed by different appliances in the series may overlap and some may be unique to a particular appliance. By way of example, a first appliance can include a first number of bite adjustment structures designed to provide a disocclusion for a number of teeth of a first jaw and/or a second jaw to help correct for at least one of overjet 1042 and overbite 1040. A second appliance can include a second number of bite adjustment structures designed to provide a disocclusion for the number of teeth of the first jaw and/or the second jaw to correct for at least one of overjet 1042 and overbite 1040. In this example, the first appliance can correct for either or both of overjet 1042 and overbite 1040 and the second appliance can correct for either or both of overjet 1042 and overbite 1040. Correction for overbite and/or overjet can include adjustments to the position of various teeth and or relative positioning of the jaws by the appliances (e.g., including adjustments affected by the number of bite adjustment structures, as described herein). Such adjustments can include intrusion, rotation, inclination, and/or disocclusion, among others.

Figure 11:
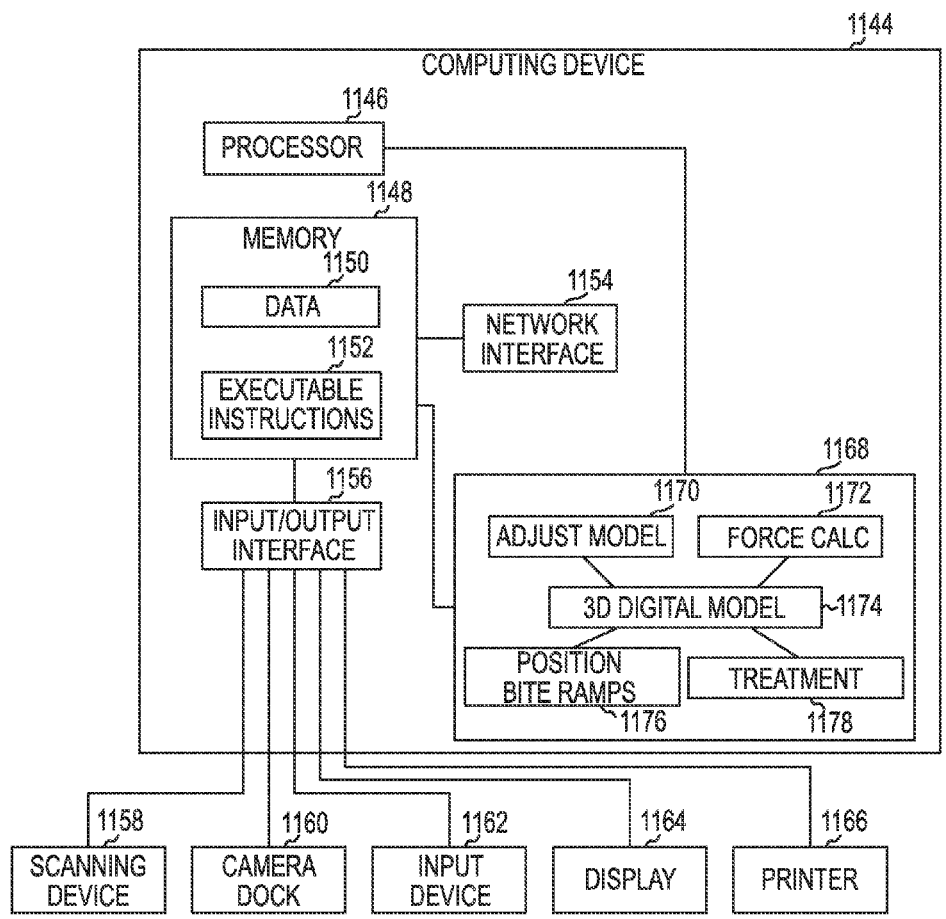
FIG. 11 illustrates a system for treatment plan specific bite adjustment structures according to one or more embodiments of the present disclosure.

FIG. 11 illustrates a system for treatment plan specific bite adjustment structures according to one or more embodiments of the present disclosure. In the system illustrated in FIG. 11, the system includes a computing device 1144 having a number of components coupled thereto. The computing device 1144 includes a processor 1146 and memory 1148. The memory can include various types of information including data 1150 and executable instructions 1152 as discussed herein.

Memory and/or the processor may be located on the computing device 1144 or off the device in some embodiments. As such, as illustrated in the embodiment of FIG. 11, a system can include a network interface 1154. Such an interface can allow for processing on another networked computing device or such devices can be used to obtain information about the patient or executable instructions for use with various embodiments provided herein.

As illustrated in the embodiment of FIG. 11, a system can include one or more input and/or output interfaces 1156. Such interfaces can be used to connect the computing device with one or more input or output devices.

For example, in the embodiment illustrated in FIG. 11, the system includes connectivity to a scanning device 1158, a camera dock 1160, an input device 1162 (e.g., a keyboard, mouse, etc.), a display device 1164 (e.g., a monitor), and a printer 1166. The processor 1146 can be configured to provide a visual indication of a digital model 1174 on the display 1164 (e.g., on a GUI running on the processor 1146 and visible on the display 1164). The input/output interface 1156 can receive data, storable in the data storage device (e.g., memory 1148), representing the digital model 1174 (e.g., corresponding to the patient's upper jaw and the patient's lower jaw).

In some embodiments, the scanning device 1158 can be configured to scan a physical mold of a patient's upper jaw and a physical mold of a patient's lower jaw. In one or more embodiments, the scanning device 1158 can be configured to scan the patient's upper and/or lower jaws directly (e.g., intraorally).

The camera dock 1160 can receive an input from an imaging device (e.g., a 2D imaging device) such as a digital camera or a printed photograph scanner. The input from the imaging device can be stored in the data storage device 1148.

Such connectivity can allow for the input and/or output of digital model 1174 information or instructions (e.g., input via keyboard) among other types of information. Although some embodiments may be distributed among various computing devices within one or more networks, such systems as illustrated in FIG. 11 can be beneficial in allowing for the capture, calculation, and/or analysis of information discussed herein.

The processor 1146, in association with the data storage device 1148, can be associated with data and/or application modules 1168. The processor 1146, in association with the data storage device 1148, can store and/or utilize data and/or execute instructions to provide a number of application modules for treatment plan specific bite adjustment structures.

Such data can include the digital model 1174 described herein (e.g., including a first jaw, a second jaw, a number of appliances, etc.). Such application modules can include an adjustment module 1170, a force calculation module 1172, a position bite adjustment structures module 1176, and/or a treatment plan module 1178.

The position bite adjustment structures module 1176 can be configured to position a number of bite adjustment structures on a corresponding number of digital teeth (e.g., anterior teeth) of the digital model 1174 of a jaw at a first stage of a treatment plan. The position module 1176 can be configured to incorporate a result of forces modeled by the force calculation module 1172 (e.g., forces used to reposition the corresponding number of digital teeth a first distance according to a first stage of the treatment plan).

The adjustment module 1170 can be configured to adjust the position of the number of bite adjustment structures on the corresponding number of digital teeth of the digital model 1174 of the jaw at a second stage of the treatment plan according to changes to the digital model 1174 of the jaw between the first stage and the second stage of the treatment plan. The adjustment module 1170 can be configured to adjust the position of the number of digital bite adjustment structures by changing a shape (e.g., size, a number of angles, etc.) and/or an attachment location of the number of digital bite adjustment structures on the corresponding number of digital teeth of the digital model of the jaw. The adjustment module 1170 can be configured to adjust a shape of the digital model 1174 of the jaw at the first stage of the treatment plan such that the corresponding one of the appliances formed thereover distributes a counterforce corresponding to the force modeled by the force calculation module 1172 to a number of posterior teeth of the user's jaw. The adjustment module 1170 can be configured to incorporate a result of forces modeled by the force calculation module 1172 (e.g., forces used to reposition the corresponding number of digital teeth a second distance according to a second stage of the treatment plan).

The force calculation module 1172 can be configured to model an inherent force applied to the number of bite adjustment structures by a user wearing a corresponding one of the appliances during the first stage of the treatment plan. The treatment plan module 1178 can be configured to create, edit, delete, revise, or otherwise modify the treatment plan (e.g., based at least in part on operation of other application modules 1168).

The digital model 1174 can be provided (e.g., via network interface 1154) for fabrication of physical models corresponding to the jaw at the first and the second stages of the treatment plan for formation of appliances thereover such that the appliances inherit a shape of the number of digital bite adjustment structures.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A system, comprising:
   a first appliance of a series of appliances to incrementally implement a treatment plan for a patient having a first jaw and a second jaw, comprising a first shell having a plurality of cavities therein to receive teeth of the first jaw;
   a first bite adjustment structure formed of a same material as the first shell and extending therefrom and having a first location with respect to a cavity of the plurality of cavities of the first shell and a first shape, said first shape comprising a first planar surface oriented at first and second angles to an occlusal plane defined by the cavities of the first shell, the first angle being about a mesial-distal axis and the second angle being about a facial-lingual axis, thereby allowing a contacting tooth of a second jaw to slide along the surface;
   a second appliance of the series of appliances, comprising a second shell having a plurality of cavities therein to receive teeth of the first jaw; and
   a second bite adjustment structure formed of a same material as the second shell and extending therefrom and having a second location with respect to a cavity of the plurality of cavities of the second shell, the second location being different than the first location, a second shape, said second shape different than the first shape.

2. The system of claim 1, the first shape and first location are based on at least one of an interface with a particular tooth of the second jaw and an orientation of a tooth over which the bite adjustment structure is positioned when the appliance is worn and the first and second jaws are in occlusion.

3. The system of claim 1, wherein the series of appliances includes a third appliance comprising a third shell having a plurality of cavities therein designed to receive teeth of the second jaw during the first stage of the treatment plan.

4. The system of claim 3, wherein the third appliance includes a third bite adjustment structure formed of a same material as the third shell and extending therefrom and interfaces with teeth of the first jaw, and wherein the third of bite adjustment structure has a shape and a location specific to the first stage of the treatment plan.

5. The system of claim 1, wherein the first of bite adjustment structure extends from cavity of the shell that receives an anterior tooth, and wherein the first bite adjustment structure is on a canine-receiving cavity, said first bite adjustment structure on the canine-receiving cavity shaped to alter an interface between the canine-receiving cavity and a corresponding tooth on the second jaw when the first appliance is worn by the patient, thereby adjusting canine guidance.

6. The system of claim 1, wherein the first bite adjustment structure extends from a cavity of the shell that receives a posterior tooth, and wherein the first bite adjustment structure provides a disocclusion between the first jaw and the second jaw when the first appliance is worn by the patient.

7. The system of claim 1, wherein the first number of bite adjustment structures extend from a number of cavities of the shell that receive anterior teeth, and wherein the first number of bite adjustment structures provide a disocclusion between the first jaw and the second jaw when the first appliance is worn by the patient.

8. The system of claim 1, wherein the series of appliances includes a third appliance comprising a third shell having a plurality of cavities therein to receive teeth of the first jaw and to reposition a number of the teeth of the first jaw, wherein the third appliance does not include a bite adjustment structure.

9. The system of claim 1, wherein the series of appliances includes:
   a third appliance comprising a third shell having a plurality of cavities therein to receive teeth of the first jaw;
   a third bite adjustment structure formed of a same material as the third shell and extending therefrom, wherein the third bite adjustment structure has a third shape and a third location specific to a third stage of the treatment plan;
   a fourth appliance comprising a fourth shell having a plurality of cavities therein to receive teeth of the second jaw; and
   a fourth bite adjustment structure formed of a same material as the fourth shell and extending therefrom and interacting with the third bite adjustment structure, wherein the fourth bite adjustment structure have a fourth shape and a fourth location specific to the third stage of the treatment plan.

10. A system, comprising:
    a first appliance of a series of appliances to incrementally implement a treatment plan for a patient having a first jaw and a second jaw, comprising a first shell having a plurality of cavities therein to receive teeth of the first jaw in a first stage of the treatment plan;
    a first bite adjustment structure formed of a same material as the first shell, extending from a first cavity of the first shell and having a first location relative to the first cavity and a first shape specific to the first stage of the treatment plan to interface with a first tooth of the second jaw to provide a disocclusion between the first jaw and the second jaw; and
    a second appliance of the series of appliances, comprising a second shell having a plurality of cavities therein to receive teeth of the first jaw in a second stage of the treatment plan;
    a second bite adjustment structure formed of a same material as the second shell, extending from a second cavity of the second shell and having a second shape different than the first shape and a second location, relative to the second cavity of the second appliance, different than the first location, relative to the first cavity of the first appliance, said second shape and said second location specific to the second stage of the treatment plan and designed to interface with a second tooth of the second jaw, different than the first tooth of the second jaw to provide a disocclusion between the first jaw and the second jaw, wherein the first bite adjustment structure extends through the occlusal plane, defining a space along the occlusal plane between the first bite adjustment structure and a part of the first appliance defining the first cavity, said first bite adjustment structure extending a distance sufficient to contact the first tooth of the second jaw, thereby providing disocclusion between the first jaw and the second jaw.

11. The system of claim 10, including a third appliance of the series of appliance, comprising a third shell having a plurality of cavities therein to receive teeth of the second jaw in the first stage of the treatment plan, wherein a cavity of the third appliance includes a surface that is contoured to receive the first bite adjustment structure.

12. The system of claim 10, wherein the first bite adjustment structure extends from a posterior cavity on a right side of the first shell; and wherein the second bite adjustment structure extends from a posterior cavity on a left side of the second shell.

* * * * *